United States Patent
Ryan et al.

(10) Patent No.: US 9,910,963 B2
(45) Date of Patent: Mar. 6, 2018

(54) MARKET MEASURES AND OUTCOMES FOR APP PRESCRIBING

(71) Applicants: Brad Ryan, Chicago, IL (US); John MacCarthy, Bourne End (GB); Glen Connery, Warminster, PA (US); Seth Reid, London (GB)

(72) Inventors: Brad Ryan, Chicago, IL (US); John MacCarthy, Bourne End (GB); Glen Connery, Warminster, PA (US); Seth Reid, London (GB)

(73) Assignee: Quintiles IMS Incorporated, Danbury, CT (US)

( * ) Notice: Subject to any disclaimer, the term of this patent is extended or adjusted under 35 U.S.C. 154(b) by 396 days.

(21) Appl. No.: 13/933,405

(22) Filed: Jul. 2, 2013

(65) Prior Publication Data
US 2015/0012283 A1     Jan. 8, 2015

(51) Int. Cl.
G06F 19/00     (2018.01)
G06Q 50/22     (2018.01)
G06Q 10/10     (2012.01)
H04W 4/00      (2018.01)

(52) U.S. Cl.
CPC ........ *G06F 19/3437* (2013.01); *G06F 19/327* (2013.01); *G06Q 10/10* (2013.01); *G06Q 50/22* (2013.01); *H04W 4/003* (2013.01)

(58) Field of Classification Search
CPC .............. G06F 19/322; G06F 19/3418; G06F 19/3406; G06F 19/3456; G06F 19/3443; A61B 2505/07; G06Q 50/22
USPC ......................................... 705/2, 3; 600/300
See application file for complete search history.

(56) References Cited

U.S. PATENT DOCUMENTS

| | | | |
|---|---|---|---|
| 7,339,891 B2* | 3/2008 | Binder | H04L 12/2697 370/231 |
| 8,073,950 B2* | 12/2011 | Goodermote et al. | 709/226 |
| 8,608,654 B2* | 12/2013 | Carlberg et al. | 600/300 |
| 8,788,282 B2* | 7/2014 | Watanabe | 705/2 |
| 8,930,213 B2* | 1/2015 | Gotlib et al. | 705/2 |
| 8,947,237 B2* | 2/2015 | Margon et al. | 340/573.1 |
| 2004/0143171 A1* | 7/2004 | Kalies | 600/300 |
| 2004/0193448 A1* | 9/2004 | Woodbridge et al. | 705/2 |
| 2005/0021519 A1* | 1/2005 | Ghouri | 707/9 |
| 2008/0109252 A1* | 5/2008 | LaFountain et al. | 705/2 |
| 2010/0268552 A1* | 10/2010 | Schoenberg et al. | 705/3 |
| 2012/0296672 A1* | 11/2012 | Bates | G06Q 50/24 705/3 |
| 2013/0138458 A1* | 5/2013 | Lorsch | 705/3 |
| 2013/0227683 A1* | 8/2013 | Bettini | G06F 21/57 726/22 |
| 2014/0089836 A1* | 3/2014 | Damani | G06F 19/3418 715/771 |
| 2014/0244296 A1* | 8/2014 | Linn et al. | 705/3 |
| 2014/0257047 A1* | 9/2014 | Sillay | A61B 5/11 600/301 |

* cited by examiner

*Primary Examiner* — Minnah Seoh
*Assistant Examiner* — Teresa Williams
(74) *Attorney, Agent, or Firm* — Fish & Richardson P.C.

(57) ABSTRACT

The disclosure generally describes computer-implemented methods, software, and systems for receiving and aggregating anonymized data reports about when prescribers provide wireless device applications to patients. The disclosure discusses ways of analyzing the data reports in combination with other electronic medical information to generate useful conclusions about scenarios in the health care process.

33 Claims, 11 Drawing Sheets

MARKET MEASURES AND OUTCOMES FOR APP PRESCRIBING

BACKGROUND

As part of the health care process, physicians or other medical care providers may suggest, request, or "prescribe" patients use a health, wellness, or disease management application as part of the patient's medical treatment. For example, such an application may be a mobile or web application.

OVERVIEW

The present disclosure relates to computer-implemented methods, software, and systems for gathering information about when patients are prescribed applications, such as wireless device applications, to help treat medical conditions. By gathering and analyzing application prescription data, implementations can measure, track, and link the application prescription data to outcomes, such as treatment outcomes or economic outcomes. The present disclosure explains how the wireless device application prescription information can be gathered and then subsequently used in a manner that provides helpful conclusions to participants in the health care process.

One computer-implemented method includes receiving via a communications network, by an analytic server, one or more data reports from one or more wireless device application providers that provide wireless device applications to patients, each data report comprising an anonymized patient identifier that identifies the patient associated with the data report, and a wireless device application identifier that identifies the wireless device application associated with the data report, wherein the wireless device application is provided to aid in the treatment of one or more medical conditions of the patient; retrieving via the communications network, by the analytic server, patient population information, comprising electronic medical information associated with a patient population to whom wireless device applications were provided, using the anonymized patient identifiers associated with each data report; organizing data reports into different data sets for analysis based on their wireless device application identifier, wherein data reports in a data set are associated with the same wireless device application identifier; analyzing the data sets and the patient population information to generate a conclusion about the impact of a wireless device application on a particular scenario; and reporting the conclusion.

Other implementations include corresponding computer systems, apparatus, and computer programs recorded on one or more computer storage devices, each configured to perform the actions of the method. A system of one or more computers can be configured to perform particular operations or actions by virtue of having software, firmware, hardware, or a combination of software, firmware, or hardware installed on the system that in operation cause or causes the system to perform the actions. One or more computer programs can be configured to perform particular operations or actions by virtue of including instructions that, when executed by a data processing apparatus, cause the apparatus to perform the actions.

The foregoing and other implementations can each optionally include one or more of the following features. In some implementations, generating the conclusion includes generating quantitative information about the impact of a wireless device application on a particular scenario. In some implementations, the analyzing may comprise comparing a characteristic of a data set in which the wireless device application was provided to a characteristic of a control set that includes members of the patient population that were not using the wireless device application. In some implementations, receiving the one or more data reports may further comprise receiving for each data report a corresponding provider identifier that identifies the wireless device application provider associated with the data report, the retrieving further retrieves provider information associated with each data report using the corresponding provider identifier associated with the data report, and the analyzing further uses the provider information to generate a conclusion about the effects of providing a given wireless device application. In some implementations, retrieving the patient information may include retrieving information about treatment outcomes for the medical conditions of the patient, and the analyzing may generate a conclusion about the effects of the wireless device application on the treatment outcomes of the one or more medical conditions. In some implementations, retrieving the patient information may include retrieving information about treatment outcomes for the medical conditions of the patient and a drug, medical device, or other therapy prescribed to the patient, and the analyzing may generate a conclusion about the effects of coadminstruction of the wireless device application the drug, medical device, or other therapy on the treatment outcomes of the one or more medical conditions. In some implementations, retrieving the patient information may include retrieving information about treatment costs for the medical conditions of the patient, and the analyzing may generate a conclusion about the effects of the wireless device application on the treatment costs of the one or more diseases. In some implementations, retrieving the patient population information may include: tracking usage information of a reconciled regiment of wireless applications by the patient population; and retrieving the tracked usage information. Tracking the usage information of a reconciled regiment of wireless device applications may include tracking the usage information of wireless device applications from more than one wireless device application providers. In some implementations, retrieving the patient population information may include retrieving reimbursement information for a particular wireless application prescribed to the patient, the reimbursement information including a payor identifier that identifies a party reimbursing the patient, as well as an extent of the reimbursement. In some implementations, organizing the data reports may further comprise filtering patients from the patent population in one or more data sets based on one or more sets of demographic attributes, and wherein the analyzing the data sets may comprise comparing a data set including patients with a first set of demographic attributes to a data set including patients with a second set of demographic attributes to generate a conclusion about the different effects of providing a given wireless device application to patients with the first set of demographic attributes and the patients with the second set of demographic attributes. Some implementations may further comprise presenting the conclusion to a physician for use in making a treatment or clinical decision for an individual patient seeking such treatment or clinical decision from the physician. Some implementations may further comprise presenting the conclusion to a payor, insurance provider or a pharmaceutical sales representative for use in making an economic, marketing, or financial decision.

The details of one or more implementations of the subject matter of this specification are set forth in the accompanying drawings and the description below. Other features, aspects, and advantages of the subject matter will become apparent from the description, the drawings, and the claims.

DETAILED DESCRIPTION

Figure 1:
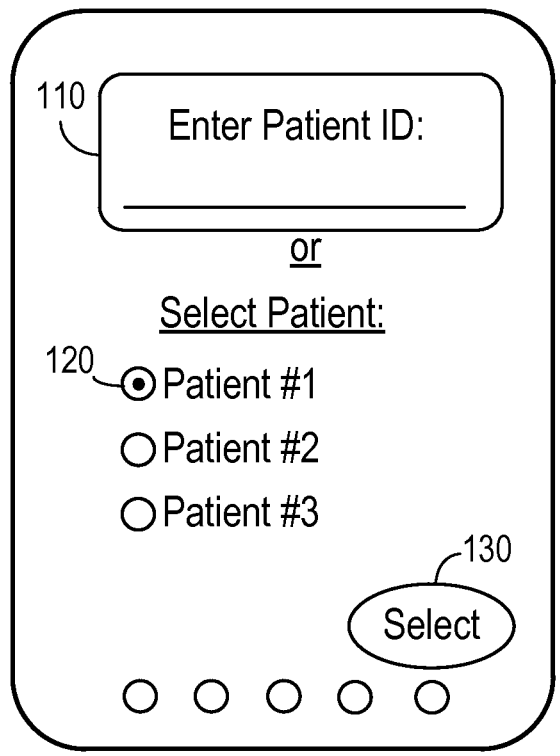
FIG. 1 is a screen shot of a user interface that allows patient selection for wireless device application distribution.

This disclosure generally describes a mechanism for capturing information on the prescribing of mobile health and web applications that physicians use in patient care. Such applications may provide a patient with the ability to track medical data, may make treatment recommendations, and so on to aid in the medical care process. Thus, such applications are therapeutic interventions and have a meaningful role in the health care process. Implementations described in this application provide a variety of ways that gathering data about how such applications are administered and prescribed can lead to useful conclusions, such as to aid in medical treatment of a patient or in making economic decisions related to the medical care progress. Gathering and using application prescription data is a new approach that offers the possibility of deriving many useful conclusions that were not previously available.

Many of the applications that are available for wireless phones and similar mobile computing devices are medical or health-related applications. Such applications may have many types of functionality that address medical or health-related problems. Using medical and health-related applications can have a wide variety of benefits for users. Users may include people or entities involved in the healthcare deployment process, and different applications might be intended for different groups of users. A medical doctor might use an application to manage medication that stores a database of drug interactions, while a patient might use an application that records and organizes information about that patient's blood sugar levels. Pharmaceutical manufacturers may distribute applications related to the medications the pharmaceutical manufacturers sell. A pharmaceutical company that sells hypertension drugs might provide an application that tracks blood pressure measurements.

When an application is prescribed to a patient at a cost being paid by a party other than the patient, a "claim" is generated and associated information is transmitted to the provider, the patient, and other relevant entities (e.g., payer, employer). The creation of a claim causes a data report with information about the prescription having taken place to be subsequently sent to an analytic infrastructure for further processing. For example, data reports corresponding to claims may be aggregated and used for market measures, outcomes research, app effectiveness ratings, and potentially reimbursement.

Applications, in general, include sets of instructions that are executed by a computing device that provide functionality. However, applications may take various forms. Some applications may be exclusively local applications that are run by a computing device and request resources from a desktop operating system. However, other applications may be executed by a mobile operating system. Yet other applications may be provided through web browsers, such as by scripting, plug-ins, or other browser extensions and add-ons that allow browsers to provide hosting capability for applications. Sometimes applications are distributed, so that their functionality is provided by multiple machines, for example in a client-server or peer-to-peer distributed architecture. Distributed functionality may be especially important in implementations in which clients are mobile devices that individual users employ to interact with an analytic platform that runs on one or more servers.

Application is a general term that refers to instructions on any computing platform to accomplish a given task. However, this specification uses the terminology "wireless device application" and "app" to refer specifically to applications that run on a mobile operating system. Often such "apps" are obtained from a centralized store. However, while this specification refers to "wireless device applications" and "apps" as being used in certain implementations, the techniques presented in this specification are generally relevant to other types of applications, as well. While many example implementations presented in the specification are directed to applications that are in fact wireless device applications, or apps, implementations can also operate in scenarios in which the applications are meant to run on a desktop or laptop PC, or are provided by web browsers.

While the approach taken to gathering such information might differ slightly, the data will essentially be useful in similar ways. For example, if a patient is prescribed access to an asthma tracking application, the significant information is that the patient now has access to that program, regardless of how the application is accessed. On the other hand, it may be especially valuable to track information about the distribution of applications that are actually wireless device applications because wireless device applications, such as those running on a smartphone or tablet, are portable and convenient to use to assist in a wide range of settings. Thus, hereinafter the specification will refer to "wireless device applications" or "apps" to denote the programs prescribed to patients to treat health conditions, but these terms do not generally exclude gathering and analyzing data about health care applications and health care-related applications that are run on other computing platforms.

Examples of prescribed apps discussed in this specification may include apps that are prescribed by a physician or other treatment provider to take care of an illness of a patient. However, sometimes health care apps may be prescribed by parties who do not directly provide treatment, as discussed above. Additionally, while the examples presented in this application are chiefly directed to situations where patients are prescribed applications, implementations may track the provision of other medical applications and draw conclusions. For example, an insurer might provide an app that provides drug interaction information to a physician. The insurance company could then track data about physicians who use the drug interaction application as compared to physicians that do not use the dug interaction application, and draw economic conclusions about whether the application leads to a cost savings, and if so, how much of a savings.

When physicians suggest, request, or "prescribe" that patients use a health, wellness, or disease management app, this prescription information may be recorded in an EMR or physician note. It is possible to capture these events and bring data together with other information about the app or patient. By doing so, the data may be measured, tracked, and linked to outcomes. The ability to measure the prescribing and reimbursement of health apps and the apps' impact on patient health is important because apps are expected to become a key element of patient treatment in the same way that drugs, devices and diagnostics are today.

Healthcare participants including health insurers and provider organizations may benefit from being able to measure wireless device application prescribing for their members and/or patients segmented by factors including patient's medical condition and demographic factors. Such parties may also want to be able to compare and/or benchmark use in their patient populations by comparison to use in other health plans and institutions.

Pharmaceutical and diagnostic companies and mobile health app publishers also may want to measure their mobile health initiatives to understand their performance as compared to that of competitors and measure the return on investment (ROI) of investments.

All of these organizations would benefit from information to assess the real world impact of mobile health initiatives in improving health outcomes and cost effectiveness. A helpful approach to providing such analytically useful evidence is the ability to capture and integrate both wireless device application prescribing information and longitudinal prescription and medical record and claims data for significant numbers of patients. Implementations may enable users to capture and analyze such evidence and information. Such analysis supports developing health economic evaluations to aid in decision-making by all healthcare organizations on investments in mobile health.

Implementations have value in that the implementations enable the integration of app prescribing data at the most granular level, such as prescribed app, patient, prescriber and payor, with information about drug prescriptions and other prescribed therapies, claims and health record data for the same patients. Having the analytic information means, for example, that implementations may evaluate whether patients prescribed a particular diabetes tracking app actually exhibit improved adherence with their medications. Similarly, implementations may evaluate whether a cohort of patients prescribed fitness or diet apps actually have a reduced cost to the healthcare system when compared to a matched control group. While this comparative data analysis may not be able to establish causation, implementations may perform statistical analysis on appropriate data to establish correlations and patterns that are highly useful conclusions.

Implementations provide an IT-enabled process which captures information on the prescription of mobile health applications by physicians for their patients in a way that enables that information to be integrated with longitudinal records about prescription and other therapies, treatment and outcomes data for analytics to determine app effectiveness and ROI.

At a high level, implementations may operate as follows. When a patient registers as a user of a wireless device app provider, a specific set of information is collected which generates a unique anonymized identifier (or ID) which is identical to the one generated when Rx or other treatment data is anonymized for the same patient. Physician registration similarly generates an identifier that enables linkage between their drug and app prescribing activity. Apps in the application catalogue may be coded using a proprietary coding model that enables their linkage to disease codes. These disease codes may be helpful because implementations may be able to establish which apps are relevant to which other therapies. For example, an app that tracks dietary cholesterol could be identified as being related to being prescribed a statin, or results from a lipid panel diagnostic.

When an application prescription is generated, information on the patient, prescribing physician, prescribed application and claims reimbursement is captured using various processes, which may differ based on how the application is provided and prescribed, as well as how much the application costs and who pays for the application.

As discussed above, generally the application environment includes a wireless device or tablet that may be used by a consumer or user. In addition there may be an application that also has a desktop or laptop component. It may be noted that the "wireless" aspect of a computing device in an implementation is not intended as limiting, and computing devices that are not easily portable may be used where appropriate and devices that are portable may communicate with some of the other portions of an implementation by using a wired connection. In general, the relevance of this aspect of the design is that the portal is hosted at a device for a user, and that the device communicates with centralized infrastructure that stores and manages information for subsequent usage and analysis.

The functionality across user devices may vary with their dimensions. There may be a limited subset of data in a mobile computing device while a more expansive subset is available across a desktop environment. Such division of functionality may be due to greater computing resources at a desktop machine than a mobile computing device due to the space, physical interface, and power limitations of the mobile computing device. In addition, the application may utilize certain authentication, confidence and/or security measures that are available through a wireless device. For example, a wireless device may be designated as belonging to a particular user. However, individual users may be associated with specific accounts that are further associated with privacy settings.

Because a developer may know that a wireless handset consumer with an account with a particular national wireless carrier may have a line of credit, that determination may be used to provide an assurance level that is not necessarily be available across other platforms, such as desktops. These confidence measures may be used to offer an expansive array of products and services. However, other security means such as a password, which may be a one-time password, biometrics, a pattern and so forth may be required in an implementation to establish the identity of a user before the user is given access privileges such as the ability to make a purchase of a medical application.

The authentication is relevant because it may be necessary for a payment to take place before the patient is allowed access to the app that the physician prescribed to the patient. These security measures may also be especially important because medical data can be quite sensitive and it may be important to protect the privacy and confidentiality of participants in the healthcare process. While it is necessary for private information to be available where such private information is needed, it is of paramount importance that only parties who are entitled to access private information have access to it, so as to comply with legal standards and so that parties who should not have access to private information are unable to exploit the information to the detriment of patients or other holders of private information.

Access to the apps and information related to the apps may be secured depending on a patient's condition. As discussed briefly above, the wireless devices and other participating devices may provide other technologies that are designed to safeguard personal identifiable information and shield the inadvertent release of personally identifiable and sensitive information, particularly in those circumstances where there is a stigmatic condition or issue involved. The app may be addressed to a particular condition or treatment regimen, such as a pharmaceutical compound or treatment regimen. Alternatively, the app may include a diagnostic component and/or interface with a Bluetooth diagnostic component that may produce diagnostic measurement information, such as blood sugar and other parameters. It may be noted that Bluetooth is only one type of interface for diagnostic components and other approaches are possible.

FIG. 1 is a screen shot of a user interface that allows patient selection for wireless device application distribution. The screen shot 100 shows a patient identification control 110 that allows a prescriber or other application provider to enter an ID of a patient who should receive the wireless device application. In general, the wireless device application provider will be characterized as a physician throughout the illustrative examples, but as will be discussed later other parties can provide wireless device applications and tracking data can provide in a similar manner. For example, the ID may be an anonymized numerical or alphanumerical ID of the patient. It is generally important that the ID be anonymized, so as to protect private health information related to the user. As an alternative, patient selection control 120 allows the prescriber to select one of several potential patients to send the wireless device application to. The prescriber can then click on the select button 130 in order to select the patient identified by patient identification control 110 or patient selection control 120. While screen shot 100 shows an implementation in which one patient is selected at a time and receives one wireless device application at a time, other implementations may allow multiple patients to be selected simultaneously or multiple wireless device applications to be selected simultaneously.

Additionally, implementations may build in additional security and authentication. In addition to the patient identification process illustrated in FIG. 1, implementations may require authentication information such as a password, biometric identification or other security information in order to allow a physician the authority to prescribe wireless device applications to a user.

Figure 2:
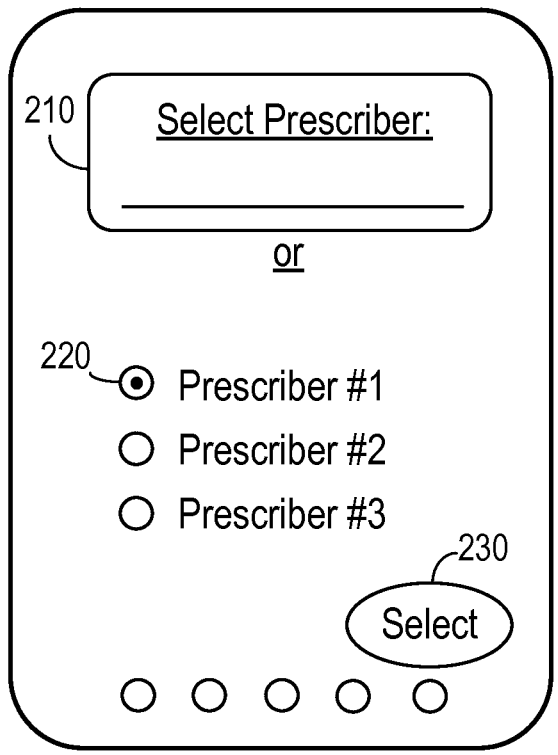
FIG. 2 is a screen shot of a user interface that allows prescriber selection for wireless device application distribution.

FIG. 2 is a screen shot of a user interface that allows prescriber selection for wireless device application distribution. FIG. 2 has similar parts to FIG. 1, but the parts allow a prescriber to identify himself or herself to an implementation, rather than a patient. Thus physician identification control 210 and physician selection control 220 are analogous to patient identification control 110 and patient selection control 120, except that physician identification control 210 and physician selection control 220 allow an implementation to identify a physician rather than a patient. Similarly, the user may use select button 230 to accept the choice of physician. It may also be noted that physician selection may require some sort of authentication as noted in connection with FIG. 1. The authentication may be especially important in the case of the physician, because not all physicians may be authorized to prescribe all apps.

Figure 3:
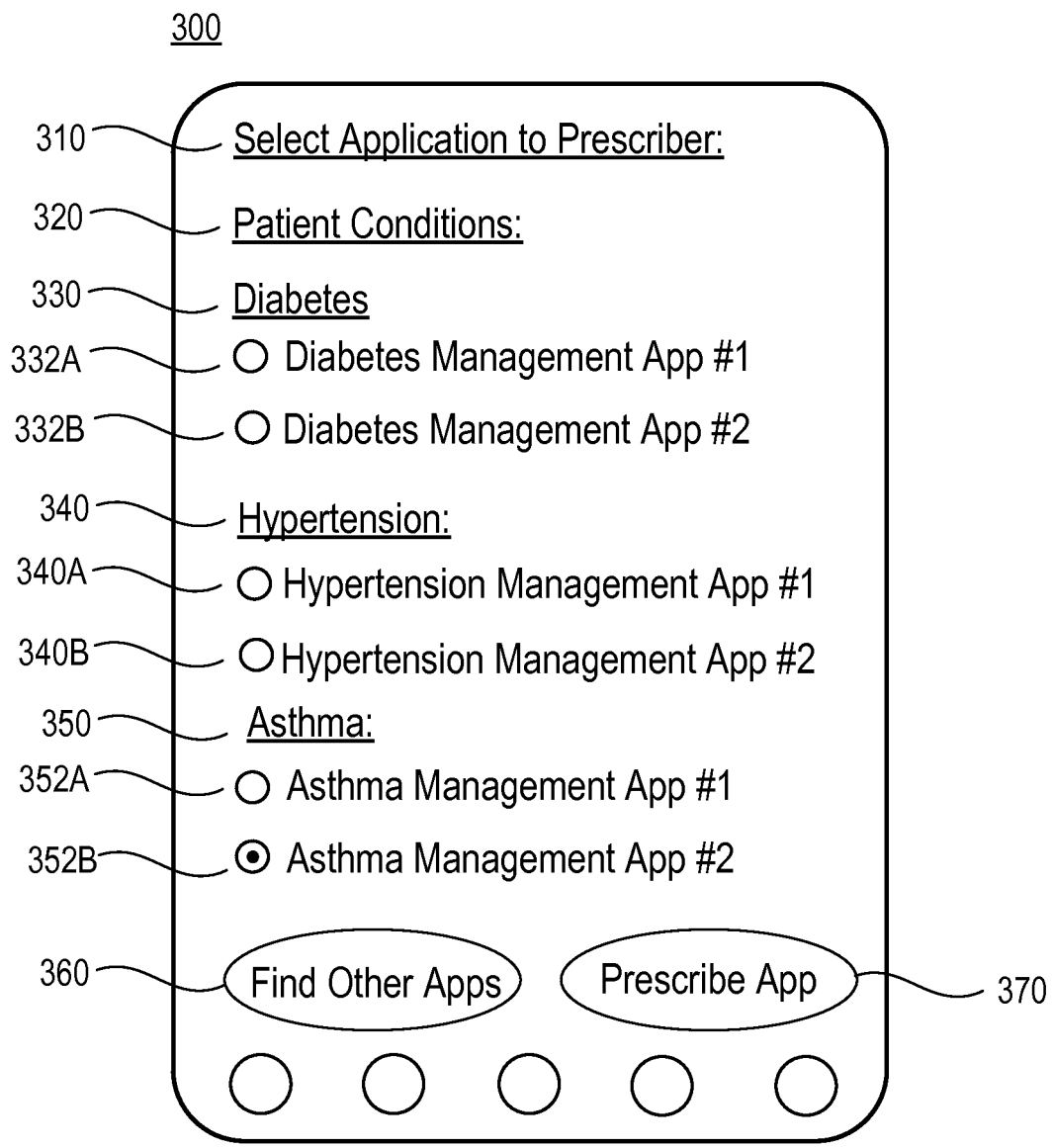
FIG. 3 is a screen shot of a user interface that allows a prescriber to select wireless device applications for distribution.

FIG. 3 is a screen shot of a user interface that allows a prescriber to select wireless device applications for distribution. Title 310 informs the prescriber to select a choice of which application to provide. Caption 320 indicates that the page lists patient conditions. The conditions shown are diabetes 330, hypertension 340, and asthma 350. The wireless device application provider suggests two wireless device applications for each condition, including diabetes management apps 332A-332B, hypertension management apps 342A-342B, and asthma management apps 352A-352B. Additionally, there is a button 360 to find other apps. Button 360 allows a prescriber to send other applications, which are not already shown, to a patient. If the prescriber invokes button 360, the prescriber will be taken to an interface in which the prescriber can identify other applications that might be appropriate to prescribe to the patient, and then prescribe the applications. For example, if a patient has high cholesterol, a prescriber might want to prescribe a hypertension treatment application even if there has not been a formal diagnosis. Additionally, prescribe app button 370 allows a prescriber to prescribe the selected application to the patient.

Figure 4:
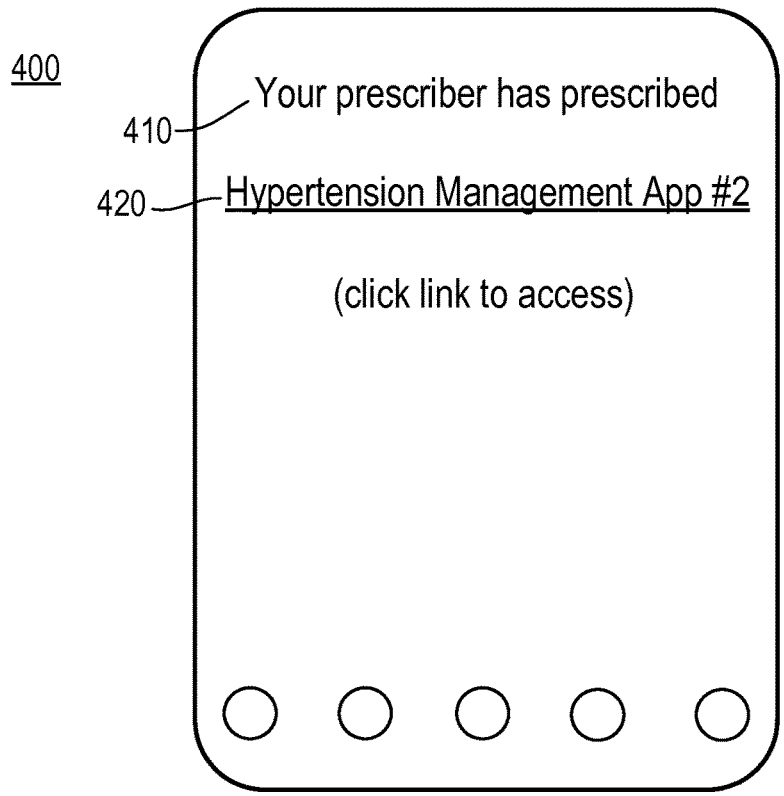
FIG. 4 is a screen shot of a user interface that allows a patient to be alerted that he or she has been prescribed a wireless device application.

FIG. 4 is a screen shot of a user interface that allows a patient to be alerted that he or she has been prescribed a wireless device application. Screen shot 400 depicts a message that alerts a user that he or she has been prescribed a wireless device application. The alert message includes a caption 410 indicating that the prescriber has prescribed an app. FIG. 4 is meant as a quick summary of a prescription decision, and more information may be provided as well. Link 420 indicates that the wireless device application that was prescribed is hypertension management app #2. By selecting link 420, the patient indicates that he or she would like to accept and access the app. The patient may either be provided the app for download by an application store, or the link may allow access to an application via the web. An aspect of purchasing an app is that there may be a charge involved. An app is assumed to be free unless the alert message specifically notifies the patient that there may be a charge involved.

Figure 5:
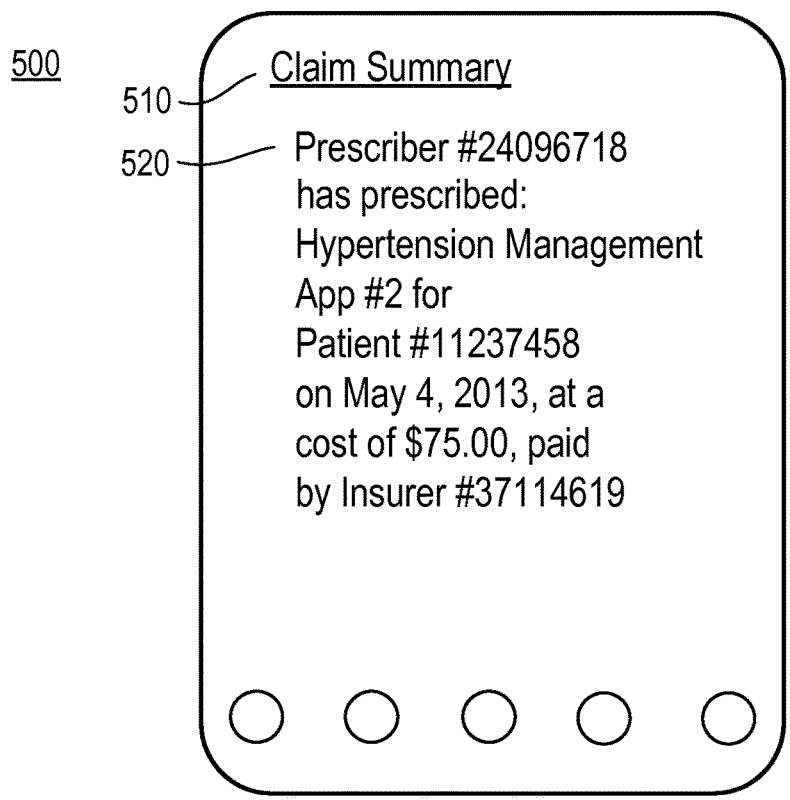
FIG. 5 is a screen shot of a user interface that shows a claim summary for wireless device application distribution.

FIG. 5 is a screen shot of a user interface that shows a claim summary for wireless device application distribution. FIG. 5 will generally be presented to the patient after the patient has accepted the prescribed wireless device application, such as in FIG. 4. Caption 510 indicates that the patient is being provided a claim summary. Claim information 520 is a listing of detailed information about the prescription of the wireless device application. As shown, claim information 520 includes information such as the ID of the prescriber, the name of the prescribed application, the name of the patient, a timestamp, a cost value, and an anonymized ID of the insurer. Claim information 520 is only an example, and claim information 520 may include additional information about health transactions or omit certain information included in FIG. 5 as being part of claim information 520.

Figure 6:
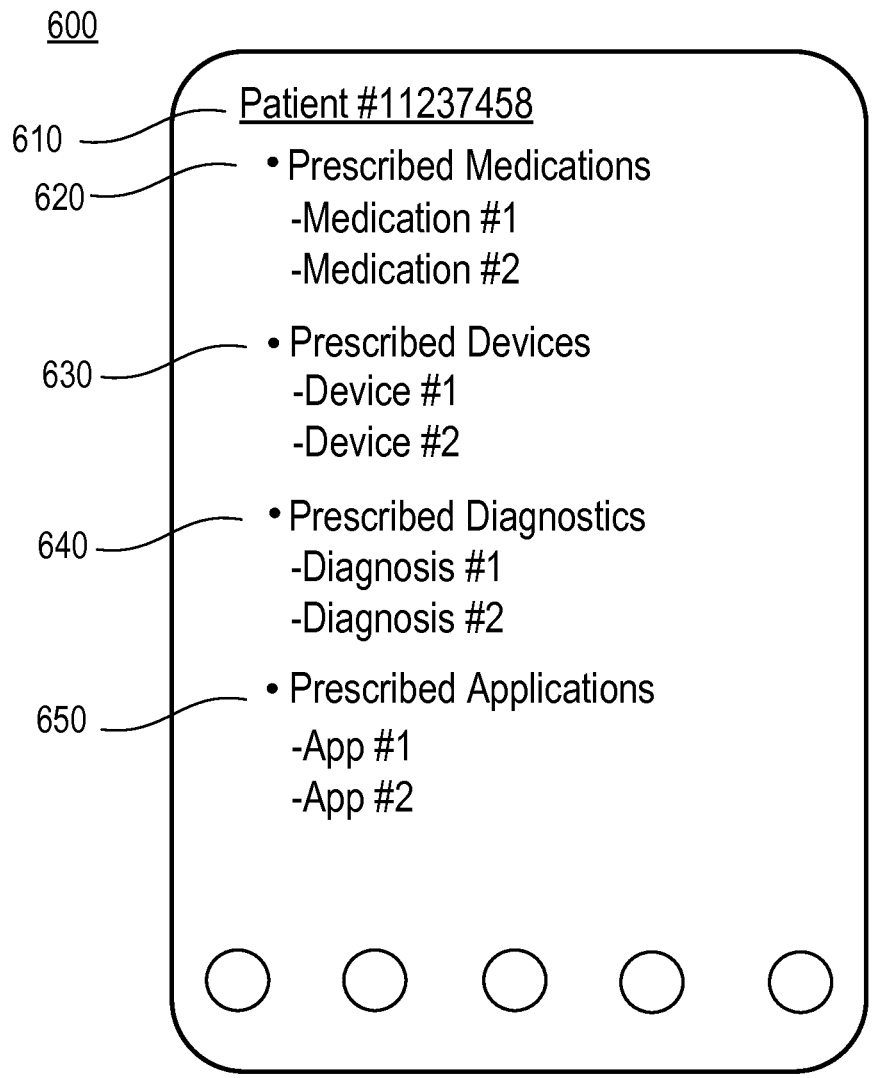
FIG. 6 is a screen shot of a user interface that shows a record of medical treatments provided to a specific patient.

FIG. 6 is a screen shot of a user interface that shows a record of medical treatments provided to a specific patient. Screen shot 600 includes a patient identifier 610. It also includes a list of prescribed medications 620, a list of prescribed devices 630, a list of prescribed diagnostics 640, and a list of prescribed applications 650. In some implementations, screen shot 600 may only include a list of prescribed applications 650. While patient identifier 610 is anonymous, FIG. 6 is an example of a presentation that show which types of treatments are co-administered. While implementations can also analyze medical treatment prescription in the aggregate, FIG. 6 organizes different therapies provided to a single patient so the prescriber can observe examples of the relationship between various therapies. For example, it might be helpful to a physician to realize that patient prescribed a certain diabetes application is also prescribed metformin rather than insulin shots. However, because the data shown in FIG. 6 is not aggregated, it is important to establish that the party viewing the consolidated information is entitled to access all of the information. For example, even if an endocrinologist treats a patient for diabetes, it may not be appropriate for the endocrinologist to know that the patient is also a user of an IUD. However, if the medical data is appropriately aggregated and anonymized, privacy is not jeopardized because conclusions do not interfere with the privacy of individual patients.

Figure 7:
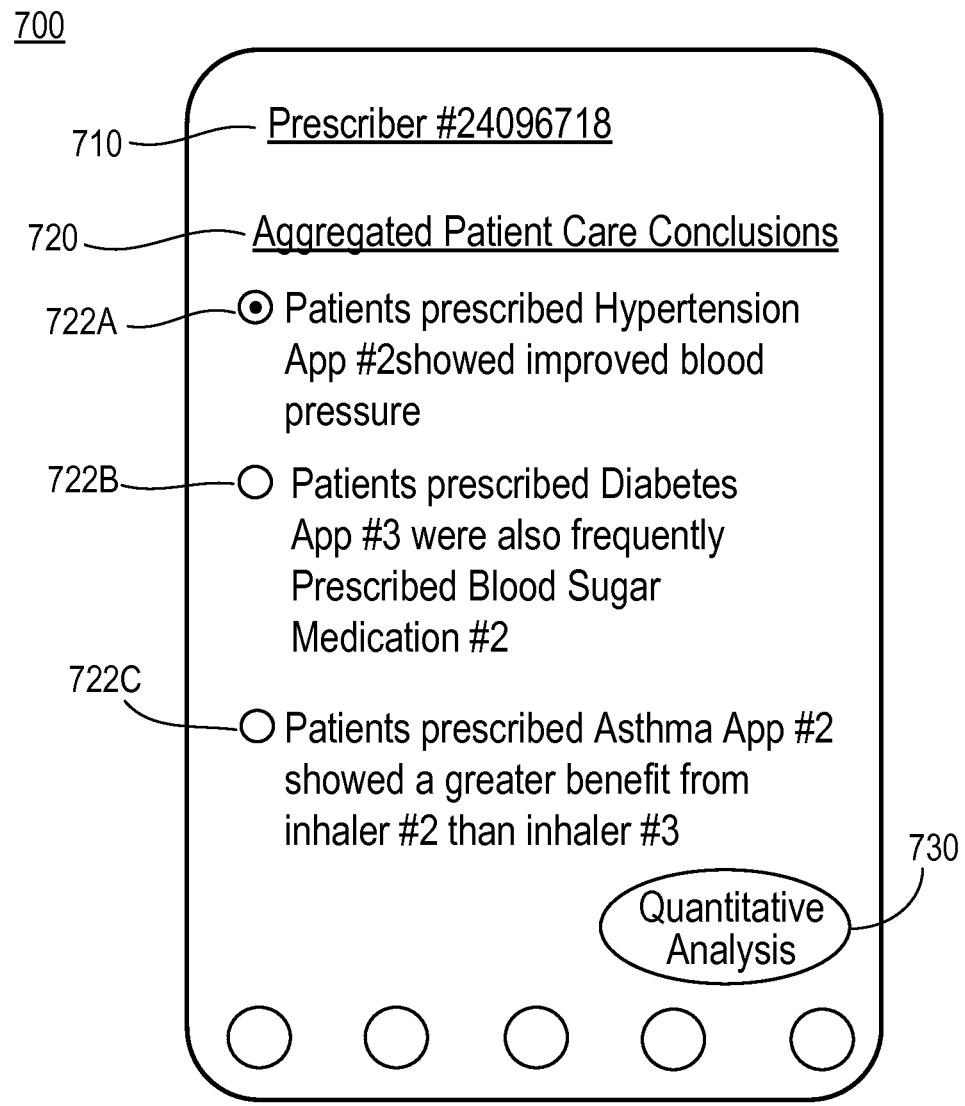
FIG. 7 is a screen shot of a user interface that draws conclusions based on wireless device application distribution for a prescriber.

FIG. 7 is a screen shot of a user interface that draws conclusions based on wireless device application distribution for a prescriber. Whereas FIG. 6 aggregates information on a patient by patient basis, FIG. 7 aggregates information across information gathered for a population of patients treated by a prescriber, as previously defined. Screen shot 700 presents a prescriber identifier 710 and a caption 720 that indicates that screen shot 700 presents aggregated patient care conclusions for the prescriber. FIG. 7 shows three example qualitative conclusions 722A-722C that are drawn based on the prescriber identifier. For example, conclusion 722A specifies that patients prescribed hypertension app #2 showed improved blood pressure. Conclusion 722B specifies that patients prescribed diabetes app #3 were also frequently prescribed blood pressure medication #2. Conclusion 722C specifies that patients prescribed asthma app #2 showed a greater benefit from inhaler #2 than inhaler #1. Additionally, button 730 allows quantitative analysis. Quantitative analysis, as will be discussed in FIG. 8 takes a qualitative conclusion about a scenario and performs statistical and mathematical analysis on the data, so that not only general conclusions are available, but a numerical categorization can also become available.

However, even with qualitative conclusions, such as those shown in FIG. 7, it is important to understand the basis of the conclusions that implementations derive. For example, conclusion 722A specifies that patients prescribed hypertension app #2 showed improved blood pressure. As will be discussed with respect to FIG. 8, such a conclusion can lead to quantitative measures. However, in order for even qualitative conclusion to be meaningful, it is necessary to specify conditions, such as which group or group of patients are being considered, what time frame is being considered, and so on. For example, conclusion 722A, that patients prescribed hypertension app #2 showed improved blood pressure, would indicate different things if a different group of patients are under consideration, or a different timeframe is under consideration. Thus, a large part of ensuring that conclusions are meaningful is that implementations need to allow parties that review the results can specify the conditions that lead to conclusions so that the conclusions are meaningful and clear.

Figure 8:
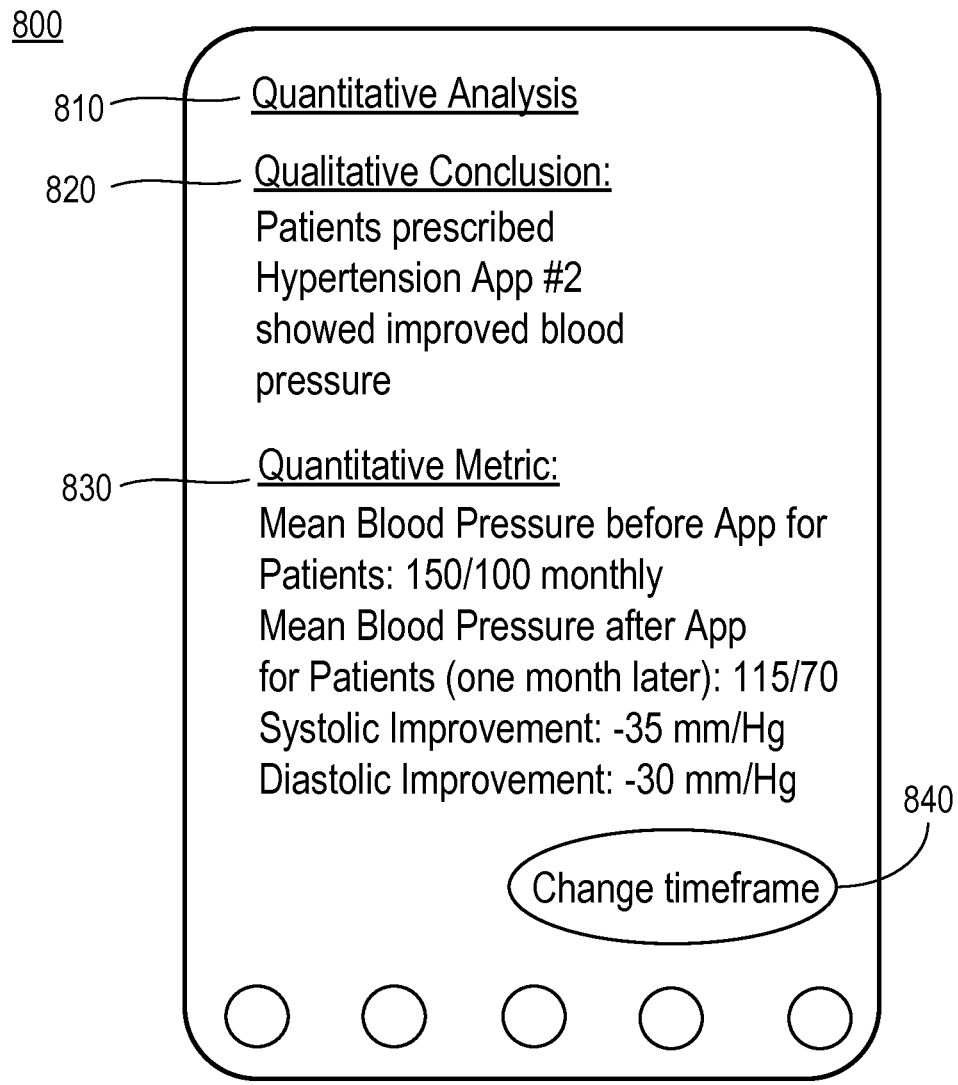
FIG. 8 is a screen shot of a user interface that draws quantitative conclusions based on wireless device application distribution for a prescriber.

FIG. 8 is a screen shot of a user interface that draws quantitative conclusions based on wireless device application distribution for a prescriber. Screen shot 800 includes a caption 810 to indicate that quantitative analysis is being performed. The qualitative conclusion 820 that is being quantified is presented in screen shot 800. For example, in FIG. 8, qualitative conclusion 820 specifies that patients prescribed hypertension app #2 showed improved blood pressure. The set of quantitative metrics 830 provides examples about how these qualitative conclusions can be transformed into numerical metrics. For example, the mean blood pressure of patients in a given population, which may be the group of patients subsequently provided wireless device application for hypertension, taken before their receipt of the wireless device application, may be 150/115 mmHg, which indicates that the patients are experiencing moderately severe hypertension. Subsequently, the mean blood pressure for the patient group, one month after receiving the application may decrease to 115/70 mmHg, which is within the normal range. Quantitative metrics 830 further establishes that this constitutes systolic improvement of −35 mmHg and diastolic improvement of −30 mmHg. Thus, quantitative metrics 830 provide information about clinical results that correlate to prescription of the application.

Additionally, change timeframe button 840 is an example of a control that helps establish conditions, as discussed above with respect to FIG. 7. By providing controls that change conditions leading up to the derivation of conclusion, more advanced analysis, which will be discussed subsequently, becomes possible. For example, FIG. 8 indicates that there a was a drop in blood pressure for patients prescribed a hypertension application, one month after receiving the application. However, there may have been a factor besides the hypertension application that accounts for this treatment outcome, such as a co-administered medication. It is possible to perform further analysis that imposes this condition on the analysis to establish more advanced correlations and suggest causations, as will now be discussed.

FIG. 8 illustrates that certain conclusions reported by implementations can be quantified, and quantifying the conclusions can make the conclusions even more meaningful. For example, with respect to conclusion 722B, other quantitative measures related to conclusion 722B may be generated. For example, conclusion 722B specifies that patients prescribed diabetes app #3 were also frequently prescribed blood sugar medication #2. Quantitative measures related to conclusion 722B might specify a specific percentage, for example, that 66% of patients prescribed diabetes app #3 were also prescribed blood sugar medication #2. Thus, rather than a qualitative measure, which includes stating that these treatments "frequently" accompany one another, quantitative analysis provides a numerical measure of the conclusion. Additionally, implementations may make it possible to provide further analysis based on the quantitative conclusions. For example, it may be possible to compare treatment outcomes for the 66% of patients who were prescribed blood sugar medication #2 along with diabetes app #3 to the 34% of patients who were not prescribed blood sugar medication #2 along with diabetes #3. By performing such analysis, it can become possible to provide conclusions that further take advantage of the data to draw helpful conclusions. For example, an implementation may analyze how fasting blood sugar levels in two patient populations change. For example, suppose that there is a group of patients with diabetes, some of whom are being treated with blood sugar medication #2 and some of whom are not being treated with blood sugar medication #2. As in the example of FIG. 8, it is possible to differentiate between groups of patient outcomes that are separated between before and after being prescribed the app. Based on the previously discussed data, it becomes possible to isolate impacts of individual variables on outcome. For example, by isolating groups of patients where all members of the group were prescribed the wireless device application, but some of the patients were also on a medication and some were not, it becomes possible to draw inferences about which parts of the treatment outcomes are likely due to the use of the medical application and which parts of the treatment outcomes are likely due simply to the effects of the medication on treatment.

Figure 9:
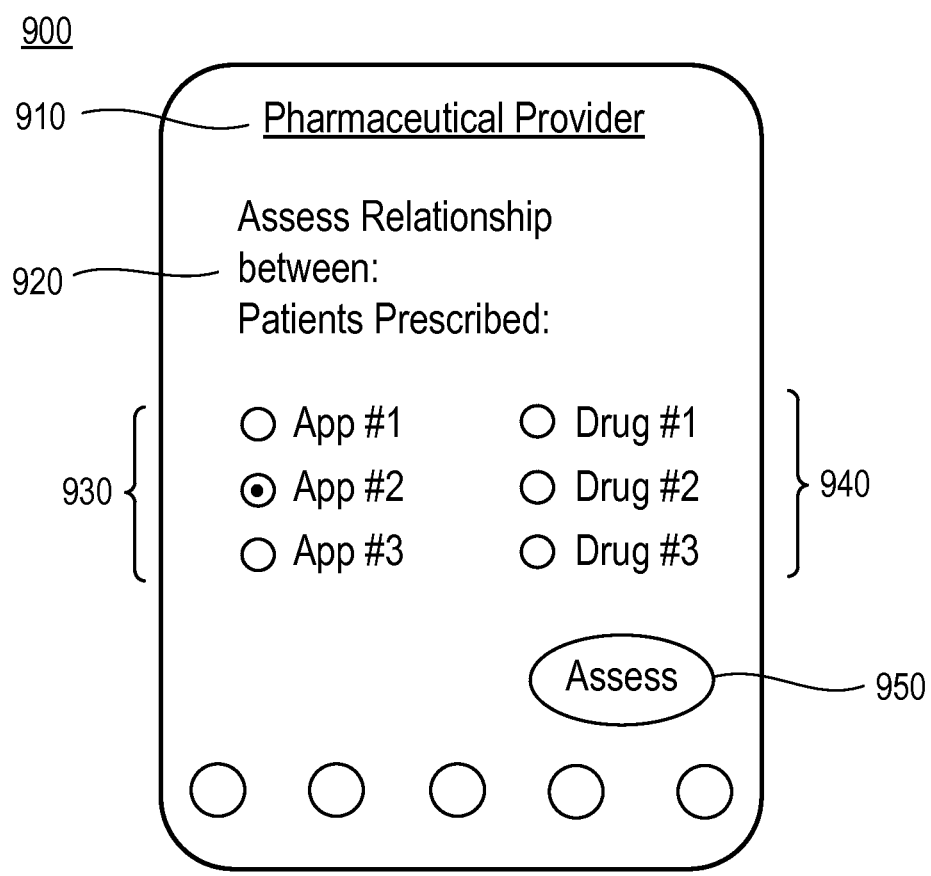
FIG. 9 is a screen shot of a user interface in which a pharmaceutical provider can determine what sort of analysis to perform based on wireless device application distribution data.

FIG. 9 is a screen shot of a user interface in which a pharmaceutical provider can determine what sort of analysis to perform based on wireless device application distribution data. Screen shot 900 includes a caption 910 that indicates that the implementation is directed to use by a pharmaceutical provider. Prompt 920 requests that the pharmaceutical provider choose an app from a group of apps 930 and a drug from a group of drugs 940. While the approach in FIG. 9 is shown as being directed towards analyzing relationships between the prescription of apps 930 and drugs 940, other implementations may perform a similar analysis between prescribed apps 930 and other therapies, such as a medical device or a diagnostic or treatment procedure. FIG. 9 shows an interface where the pharmaceutical provider can select an app and a drug to infer relationships between. In the interface depicted, the pharmaceutical provider selects an app from the group of apps 930 and a drug from the group of drugs 940 and then selects the assess button 950 to draw conclusions about the data available for the selected app and how the selected app relates to the selected drug. While FIG. 9 only shows the selection of one app and its relationship to one drug, multiple approaches are possible, and some implementations may provide the ability to compare multiple apps with multiple drugs to draw even more complicated inferences and conclusions.

Figure 10:
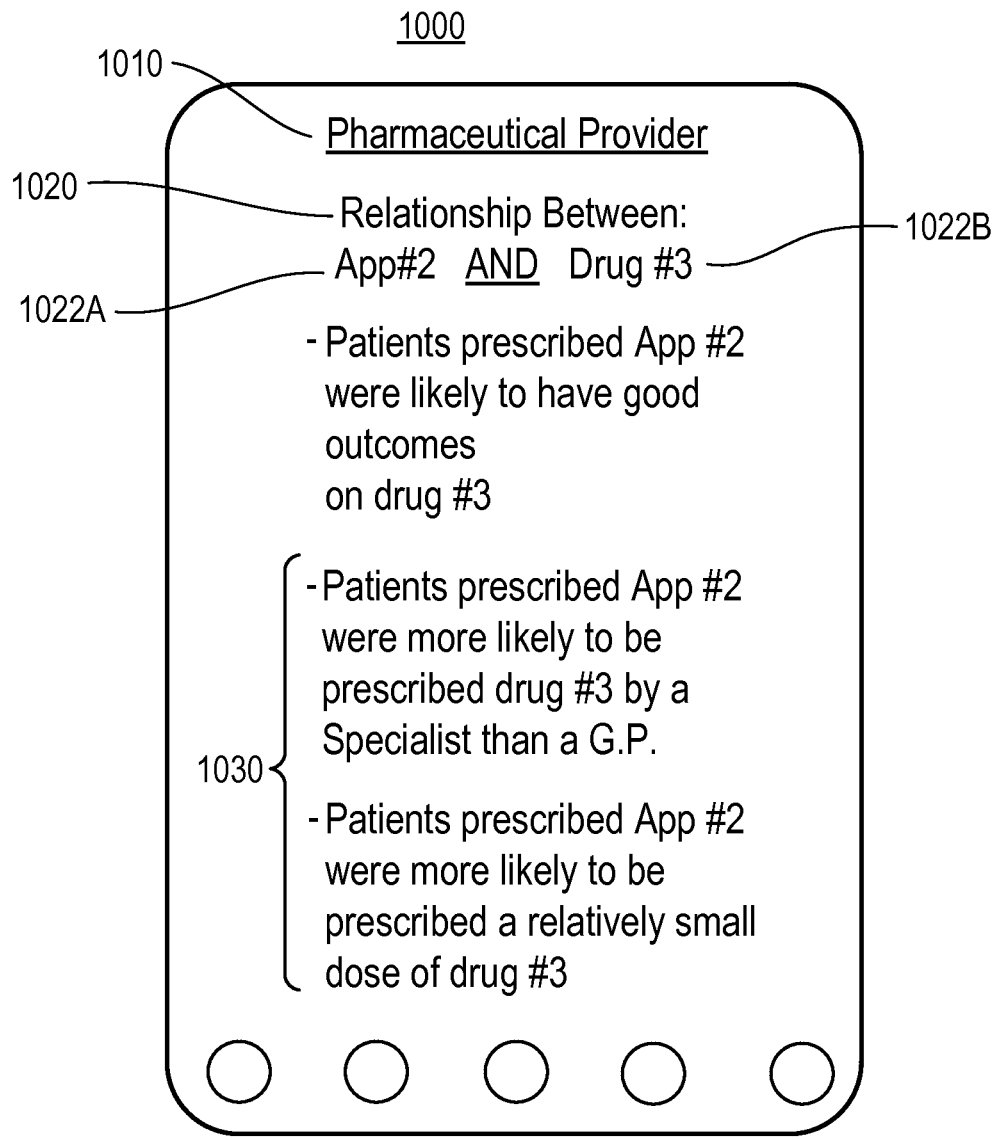
FIG. 10 is a screen shot of a user interface that draws conclusions based on wireless device application distribution for a pharmaceutical provider.

FIG. 10 is a screen shot of a user interface that draws conclusions based on wireless device application distribution for a pharmaceutical provider. Screen shot 1000 includes a caption 1010 that indicates that the implementation is for the use of a pharmaceutical provider. Caption 1020 identifies that the analysis is the relationship between a first therapy 1022A, App #2, and a second therapy 1022B, Drug #3. FIG. 10 then presents a series of inferences as inferences 1030. As discussed before, inferences 1030 include several qualitative conclusions, including "patients prescribed app #2 were like to have good outcomes on drug #3," "patients prescribed app #2 were more like to be prescribed drug #3 by a specialist than a G.P.," and "patients prescribed App #2 were more likely to be prescribed a relatively small dose of drug #3." As noted before, these conclusions may be drawn by performing appropriate statistical analyses of patient populations and the medical data associated with the patient populations. Additionally, as shown in FIG. 8, some of these conclusions can be considered based on their quantitative effects. For example, "patients prescribed App #2 were more likely to be prescribed a relatively small dose of drug #3" may also be expressed as the quantitative conclusion that patients prescribed drug #3 without being prescribed app #2 may have an average daily dose of drug #3 of 200 mg, while patients prescribed drug #3 along with app #2 might have an average daily dose of 100 mg.

Figure 11:
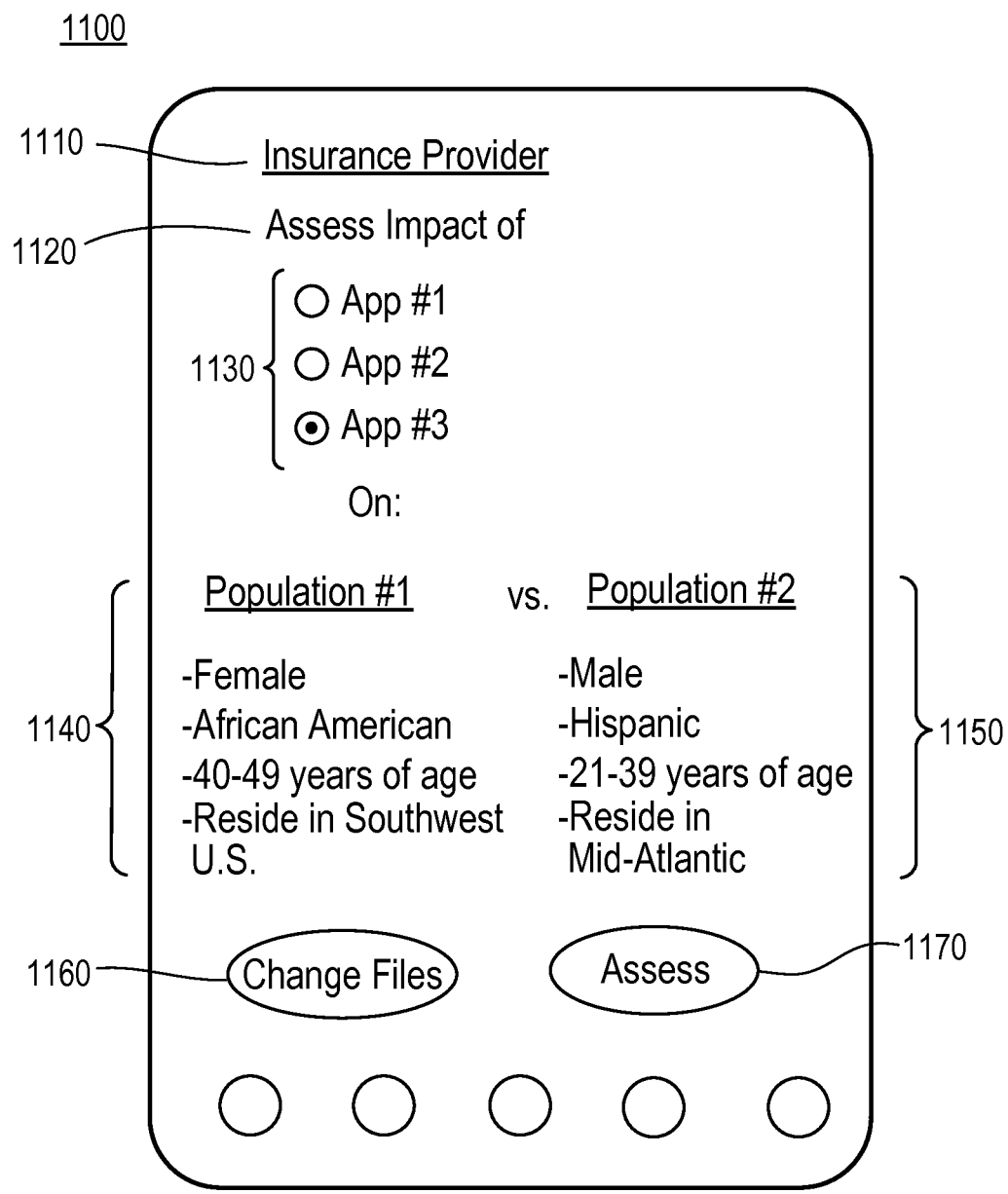
FIG. 11 is a screen shot of a user interface in which an insurance provider can determine what sort of analysis to perform based on wireless device application distribution data.

FIG. 11 is a screen shot of a user interface in which an insurance provider can determine what sort of analysis to perform based on wireless device application distribution data. Screen shot 1100 in FIG. 11 has a caption 1110 that shows that the implementation is designed to help an insurance provider. Label 1120 indicates that the implementation is designed to assess the impact of one of a set of apps 1130 on two populations, population #1 1140 and population #2 1150. The populations are groups produced by placing demographic filters on an overall population. For example, the overall population might include patients insured by a given insurance provider. For example, population #1 includes female African-Americans, who are 40-49 years of age that reside in the Southwest U.S. Population #2 includes male Hispanic individuals, who are 21-39 years of age, who reside in the Mid-Atlantic U.S. There is a change filters button 1160 that enables the user who wishes to perform demographic analysis, such as the insurance provider, to change the filters to determine which members of the overall population to include in the subpopulation. When the user invokes the assess button 1170, implementations are able to draw conclusions about the effects of the apps based on populations that are chosen based on demographic variables.

Figure 12:
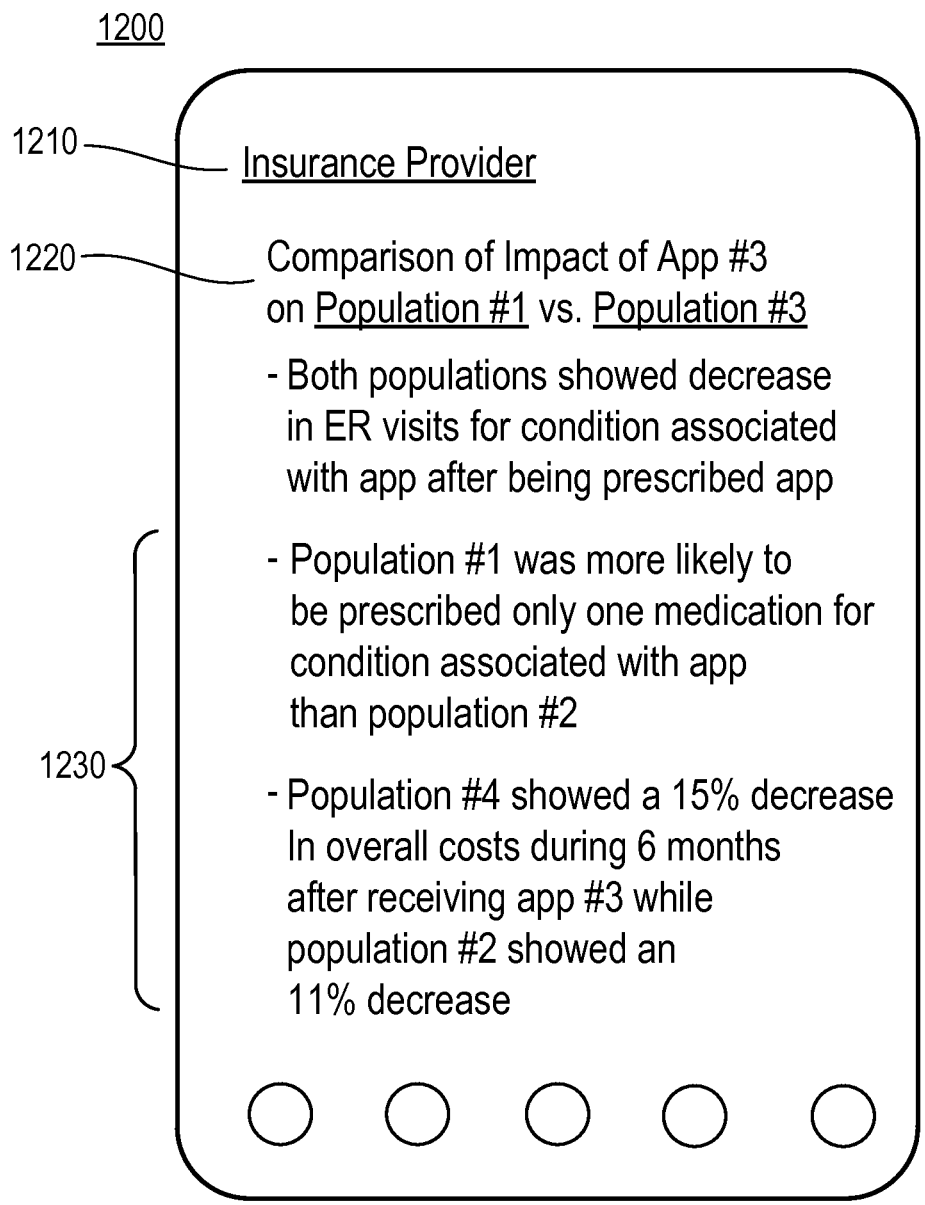
FIG. 12 is a screen shot of a user interface that draws conclusions based on wireless device application distribution for an insurance provider.

FIG. 12 is a screen shot of a user interface that draws conclusions based on wireless device application distribution for an insurance provider. Screen shot 1200 shows a caption 1210 that identifies that the implementation is being used by an insurance provider. Caption 1220 indicates that conclusions 1230 are conclusions that compare the impact of App #3 on Population #1 vs. Population #2, as indicated in FIG. 11. Conclusions 1230 are conclusions that stem from comparing the health data associated with demographic populations to one another. For example, three conclusions provided in FIG. 12 are that both populations showed a decrease in ER visits for the condition associated with the app after begin prescribed app. This conclusion is an example of a conclusion that might be drawn on a common effect of the app for both populations. For example, a dietary app that helps users manage cholesterol consumption in their diets might minimize ER visits for both populations. As noted previously, it may be appropriate to quantify the impact of the app. The dietary app just discussed might result in a 15% decrease in ER visits for one population, and a 40% decrease in ER visits for another population. Indeed, the resulting conclusions from comparing populations may be quite complicated and require sophisticated analysis of the available data. For example, population #1 might show a 15% decrease after one month, followed by a 25% decrease after two months, while population #2 might have a 10% decrease after the first month, followed by a 30% decrease after two months.

FIG. 12 also includes additional conclusions that might be derived from comparing the populations from FIG. 11. For example, FIG. 12 illustrates a comparative conclusion, which is that population #1 was more likely to be prescribed only one medication for the condition associated with the app than population #2. Of course, there may be a wide range of causes and effects related to this conclusion, but such a correlation may be useful to an insurance provider that is trying to understand how best to pay for prescription drug coverage for its clients. However, it may be desirable to associate such conclusions with other information to draw conclusions to make decisions. For example, it may be helpful to know that while population #1 is more likely than population #2 to be treated with only one medication, it may also be helpful to gather information which specific medications are prescribed, or specific costs associated with the different medication regiments from each population.

FIG. 12 also includes the conclusion that population #1 showed a 15% decrease in overall costs during 6 months after receiving app #3, while population #2 showed an 11% decrease in overall costs. This is a simple quantitative conclusion that is very helpful to a party such as an insurance provider. It shows that not only is distributing an application is likely to help manage costs, but provides a quantitative measure of how much, and which demographic might obtain the best results from being prescribed a given application.

FIGS. 1-12 are screenshots of a sample user interface for an example system for gathering and analyzing information about distribution of wireless device applications. However, it should be remembered that these are just samples of ways in which information related to distributing the wireless device applications may be utilized. As discussed throughout this specification, implementations track and gather information about individual transactions, in which wireless device application providers give access to individual patients so that the patients are able to use the applications to help manage health problems. The information should be anonymized, so as to protect the privacy and confidentiality of participants in the health care process.

However, as discussed with respect to the above examples, a wealth of conclusions may be drawing by analyzing the new data of tracking wireless device application transactions and combining the transaction data with other information that is already included in EMR systems. For example, as discussed above, there may be a large amount of information stored electronically about patients, physicians and health care providers, pharmaceutical companies, insurance companies, treatment outcomes, medication records, diagnostics, medical devices, etc. By performing analytics that combine the new data related to wireless device applications with other information to draw conclusions about different scenarios, implementations offer many powerful features. Scenarios, as used herein, may refer to any combination of clinical conditions. The clinical conditions may include patient characteristics such as age, gender, race, family history, occupational risk, prior history, etc, The clinical conditions may also include treatment parameters such as dosing, physical therapy, wellness training, etc. After analyzing the data, implementations can reports that allow users to review the conclusions to help understanding and decision-making as part of the medical care process.

Additionally, in some implementations, the reports generated may be either dynamic or static. The reporting may generate a report that includes data presented in one or more static formats (e.g., a chart, a graph, or a table) without providing any mechanism for altering the format and/or manipulating the data presented in the report. In such an implementation, the data presentation is generated and saved without incorporating functionality to update the data presentation. In some implementations, the reporting provides a static report in a PDF, spreadsheet, or XML format. Such a format generally provides an understanding of the report as textual data or a visualization, but other forms of presenting conclusions such as audio, video, or an animation are not excluded as potential results.

Additionally or alternatively, the reporting may generate a report that includes controls allowing a user to alter and/or manipulate the report itself interactively. For example, the reporting system may provide a dynamic report in the form of an HTML document that itself includes controls for filtering, manipulating, and/or ordering the data displayed in the report. Moreover, a dynamic report may include the capability of switching between numerous visual representations of the information included in the dynamic report. Additionally, users may request a static or dynamic report to organize the data to meet their data needs, as discussed.

Figure 13:
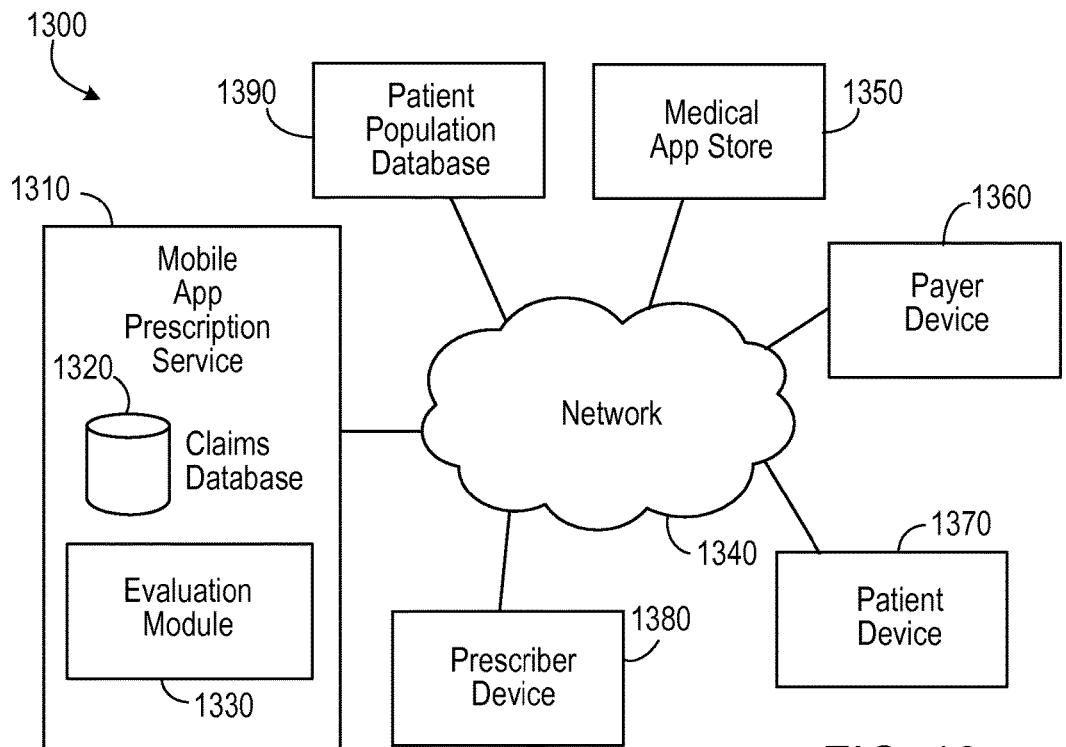
FIG. 13 is a block diagram illustrating an example system for gathering and analyzing information about distribution of wireless device applications.

FIG. 13 is a block diagram illustrating an example system for gathering and analyzing information about distribution of wireless device applications. FIG. 13 shows a computing system 1300 that includes other systems that provide the functionality of implementations. For example, mobile app prescription service 1310 performs many of the functions of implementations. Mobile app prescription service 1310 includes claims database 1320 and evaluation module 1330. Mobile app prescription service 1310 interacts with other systems through network 1340. The other systems may include a medical app store 1350, a payor device 1360, a patient device 1370, a prescriber device 1380, and a patient population database 1390. These machines interact to provide the functionality presented earlier in connection with FIG. 12 and as will be now discussed in connection with the process illustrated in FIG. 14. However, overall transactions are initiated when prescriber device 1380 indicates to medical app store 1350 that it is appropriate to provide a patient with access to a wireless device application at patient device 1370. As illustrated in FIG. 4, the patient is given access to the app from medical app store 1350. Additionally, a payor device 1360 may participate in the transaction to help manage the billing process.

After an app is successfully prescribed, information about the claim, such as that illustrated in FIG. 5, may be transmitted via network 1340 to mobile app prescription service 1310, which can store the claim information in claims database 1320. Subsequently, evaluation module 1330 processes data from claims database 1320 and also accesses patient population database 1390. Patient population database 1390 includes other information about patients, as discussed above, that may be used in conjunction with the claims from claims database 1320 to draw useful conclusions based on the application prescription data as well as other information related to the patient population. In FIG. 13, patient population database 1390 is portrayed as a centralized database on the cloud that evaluation module 1330 of mobile app prescription service 1310 is able to access through network 1340. However, the information in patient population database 1390 may also be stored and/or aggregated locally within mobile app prescription service 1310.

Thus, evaluation module 1330 accesses information about claims in combination with other data about the patient population, allowing evaluation module 1330 to derive meaningful, helpful conclusions by analysis, as discussed above.

Figure 14:
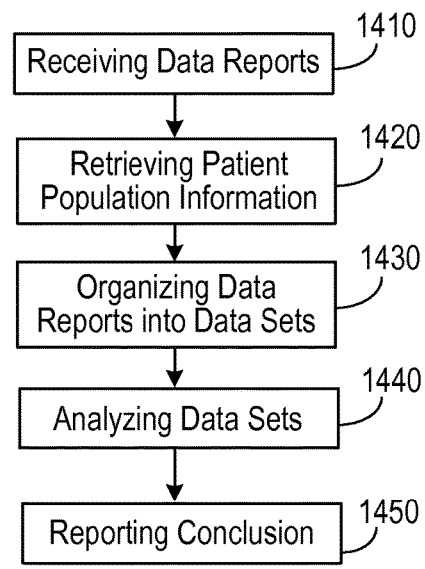
FIG. 14 is a flowchart of a process for gathering and analyzing information about distribution of wireless device applications.

FIG. 14 is a flowchart of a process for gathering and analyzing information about distribution of wireless device applications.

At block 1410, data reports are received. More specifically, one or more data reports are received via a communications network, by an analytic server, from one or more wireless device application providers that provide wireless device applications to patients, each request comprising an anonymized patient identifier that identifies the patient associated with the data report, and a wireless device application identifier that identifies the wireless device application associated with the data report, wherein the wireless device application is provided to aid in the treatment of one or more medical conditions of the patient. In the context of FIG. 13, mobile app prescription service 1310 may receive such a data report form medical app store 1350 and store information about the data report in claims database 1320. The data reports may be generated when prescriber device 1380 prescribes a wireless device application to patient device 1370. Additionally, payor device 1360 may participate by contributing funds to facilitate the performance of the transaction. In some situations, payor device 1360 may be patient device 1370, if the patient pays for his or her own application, or there may no payor device 1360 if the application is free. Often payor device 1360 will be an insurance company.

At block 1420, patient population information is retrieved. More specifically, patient population information is retrieved via the communications network, by the analytic server, comprising electronic medical information associated with a patient population to whom wireless device applications were provided, using the anonymized patient identifiers associated with each data report. In the context of FIG. 13, evaluation module 1330 of mobile app prescription service 1310 determines from claims database 1320 patient identifiers that were provided applications. Based on this set of identifiers, evaluation module 1330 can access additional information about patients prescribed applications from patient population database 1390. As discussed previously, the accessed information might include, for example, information about treatment outcomes for patients that are prescribed applications. However, the patient population information that is retrieved need not be limited only to patients that are specifically provided wireless device applications. For example, it may be desirable to retrieve additional patient population information from patient population database 1390 to use for comparison when analyzing the data. For example, implementations may retrieve information about diabetics who were prescribed a blood sugar tracking app to determine the effects of the app on their treatment. However, implementations may also retrieve information about diabetics who were not prescribed the app in order to use as a control group for comparison purposes. In general, the type of patient population information retrieved from patient population database 1390 will vary based on the type of conclusions and analysis a user would like to do.

At block 1430, data reports are organized into data sets. More specifically, data reports are organized into different data sets for analysis based on their wireless device application identifier, wherein data reports in a data set are associated with the same wireless device application identifier. In the context of FIG. 13, evaluation module 1330 may perform the organization on the data reports in claims database 1320. By grouping the data reports in to data sets based on application identifier, the data for each application is aggregated together. Because the data is aggregated, it becomes possible to draw conclusions about the effects of wireless device applications across a population without jeopardizing the privacy of individual users. Furthermore, additional organization of the data reports may occur. For example, the data reports may be further organized prior to analysis based up related information, such as demographics of the patients who received apps, or other information such as co-administered medications or treatment outcomes.

At block 1440, the data sets are analyzed. More specifically, the data sets and the patient population information are analyzed to generate a conclusion about the impact of a wireless device application on a particular scenario. Many examples of analysis have been presented in connection with FIGS. 1-12. As noted previously, these conclusions may be quantitative or qualitative. Additional aspects of what conclusions may be generated are discussed below. In general, the analysis itself is performed at evaluation module 1330 of mobile app prescription service 1310.

At block 1450, the conclusion is reported. For example, the conclusion may be displayed at a device of a participant in the medical care process. Examples of reporting the conclusion are shown in FIGS. 7, 8, 10 and 12.

Additionally, various implementations include a variety of optional features and functionality. As discussed, in some implementations, generating the conclusion includes generating quantitative information about the impact of a wireless device application on a particular scenario. In such implementations, the mathematical and statistical analysis performed on the analyzed data yield specific numerical results that provide specific metrics of relationships between the information handled by implementations.

In some implementations, the analyzing comprises comparing a characteristic of a data set in which the wireless device application was provided to a characteristic of a control set that includes members of the patient population that were not using the wireless device application. By comparing a data set that was provided the application to a control data set that was not provided the application, it is possible to help isolate and identify effects on outcomes that stemmed from the prescription of the application, as opposed to other effects. Examples of this feature have been provided previously. For example, the characteristic may be an average change in blood pressure, for patient populations with and without a blood pressure tracking app.

In some implementations, receiving the one or more data reports further comprises receiving for each data report an anonymized provider identifier that identifies the wireless device application provider associated with the data report, the retrieving further retrieves provider information associated with each data report using the anonymized provider identifier associated with the data report, and the analyzing further uses the provider information to generate a conclusion about the effects of providing a given wireless device application. For example, this feature might entail gathering a group of patients prescribed an app by one doctor, and another group of patients prescribed an app by another doctor. Comparing the information for these groups may lead to conclusions that one doctor is making better use of an application than another, or more generalized conclusions, like that the application provides better treatment outcomes when provided by a specialist rather than a general practitioner, or causes greater cost savings when provided by an in-network physician than an out-of-network doctor.

In some implementations, retrieving the patient information includes retrieving information about treatment outcomes for the medical conditions of the patient, and the analyzing generates a conclusion about the effects of the wireless device application on the treatment outcomes of the one or more medical conditions. Examples of this feature are provided above, such as the effects of an app on hypertension. In some implementations, retrieving the patient information includes retrieving information about treatment outcomes for the medical conditions of the patient and a drug, medical device, or other therapy prescribed to the patient, and the analyzing generates a conclusion about the effects of coadministration of the wireless device application the drug, medical device, or other therapy on the treatment outcomes of the one or more medical conditions. Examples of this feature are provided above, such as the effects of an app in combination with a certain medication. In some implementations, retrieving the patient information includes retrieving information about treatment costs for the medical conditions of the patient, and the analyzing generates a conclusion about the effects of the wireless device application on the treatment costs of the one or more diseases. Examples of this feature are provided above, such as analyses for an insurance company in FIG. 12 about the effects of providing an app on treatment costs. In some implementations, organizing the data reports further comprises filtering patients from the patent population in one or more data sets based on one or more sets of demographic attributes, and wherein the analyzing the data sets comprises comparing a data set including patients with a first set of demographic attributes to a data set including patients with a second set of demographic attributes to generate a conclusion about the different effects of providing a given wireless device application to patients with the first set of demographic attributes and the patients with the second set of demographic attributes. FIGS. 11-12 provide an example of this feature. Some implementations further comprise presenting the conclusion to a physician for use in making a treatment or clinical decision. For example, the conclusion may indicate that a patient with epilepsy who is also prescribed one anticonvulsant should be prescribed one epilepsy management app, while a patient with epilepsy who is prescribed another anticonvulsant should be prescribed another epilepsy management app. Some implementations further comprise presenting the conclusion to a payor, insurance provider or a pharmaceutical sales representative for use in making an economic, marketing, or financial decision. For example, observing patterns in how an acne management app is prescribed may suggest that a pharmaceutical sales representative might want to market an acne management drug to a dermatologist rather than a general practitioner.

Implementations may use the medical data for a wide variety of purposes, and the use of the medical data need not be exclusively limited simply to providing diagnoses or treatment recommendations. Indeed, as has been discussed extensively throughout this application, the medical data may be used by an application such as the second medical application to take advantage of many helpful conclusions that can be derived from the medical data, both with respect to that specific user and with respect to larger populations to which the user belongs. For example, such conclusions may be used to help make business decisions.

Thus, while privacy concerns need to be respected, medical data about individual users can be used not only for treatment, but also for other purposes including medical and pharmaceutical research, and also other applications ranging from law enforcement to marketing. Additionally, it is possible to compare medical data for individual users to medical data that has been aggregated for groups of users. While this approach has been discussed above, it is possible to aggregate data for populations of users, and obtain statistics such as various averages or other metrics about the population, and derive conclusions based on such comparisons. Examples of such uses of the data have been discussed above. In general, while implementations may use the medical data and its context to improve medical care recommendations and outcomes, that is not the only use of the medical data and implementations should be understood to include any use of the medical data that is helpful to a participant in the health care process, that may be provided by the operation of the second medical application on the medical data.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A method of analyzing wireless device application data comprising:
   receiving via a communications network, by an analytic server, one or more data reports from one or more wireless device application providers that provide wireless device applications to patients, each data report comprising an anonymized patient identifier that identifies a patient associated with the data report, and a wireless device application identifier that identifies the wireless device application discussed by the data report, wherein the wireless device application has been prescribed by a healthcare professional to aid in the treatment of one or more medical conditions of the patient and wherein the wireless device application is configured to track physiologic parameters of the patient;
   decoding, by the analytic server, the one or more data reports to retrieve, for a given data report, the anonymized patient identifier as well as the corresponding wireless device application identifier;
   retrieving via the communications network, by the analytic server, patient population information solely using the decoded anonymized patient identifier associated with each data report, the patient population information comprising electronic medical information associated with a patient population to whom more than one wireless device applications were provided;
   merging data reports to generate data sets based on the retrieved patient population information associated with the patient population to whom a particular wireless device application has been provided, such that each data set is instantaneously generated and only includes data reports associated with the same wireless device application identifier and identified solely through the anonymized patient identifier; and
   analyzing the data sets and the patient population information to determine the impact of each wireless device application from the more than one wireless device applications on managing the treatment of the one of more medical conditions across cohorts of patients without jeopardizing each patient's privacy when a first cohort of patients with a given condition who have received a particular wireless device application in addition to a regular treatment is compared to a second cohort of patients with the given condition who have received the regular treatment but without the particular wireless device application to determine an improved adherence to the regular treatment when the regular treatment is combined with the particular wireless device application.

2. The method of claim 1, wherein determining the impact of a wireless device application on managing the treatment of the one of more medical conditions includes generating quantitative information about the impact of the wireless device application on managing the treatment of the one of more medical conditions between the first cohort of patients and the second cohort of patients by virtue of a statistically different physiologic parameter being tracked by the wireless device application.

3. The method of claim 1, wherein the analyzing comprises comparing a characteristic of a data set in which the particular wireless device application was provided to a characteristic of a control set that includes members of the patient population that were not using the particular wireless device application.

4. The method of claim 1, wherein receiving the one or more data reports further comprises receiving for each data report a corresponding provider identifier that identifies the wireless device application provider associated with the data report, the retrieving further retrieves provider information associated with each data report using the corresponding provider identifier associated with the data report, and the analyzing further uses the provider information to determine the effects of providing a given wireless device application.

5. The method of claim 1, wherein retrieving the patient population information includes retrieving information about treatment outcomes for the medical conditions of the patient population, and the analyzing determines the effects of the particular wireless device application on the treatment outcomes of the one or more medical conditions.

6. The method of claim 1, wherein retrieving the patient population information includes retrieving information about treatment outcomes for the medical conditions of the patient population and a drug, medical device, or other therapy prescribed to the patient population, and the analyzing determine the effects of coadminstruction of the wireless device application, the drug, the medical device, or other therapy on the treatment outcomes of the one or more medical conditions.

7. The method of claim 1, wherein retrieving the patient population information includes retrieving information about treatment costs for the medical conditions of the patient population, and the analyzing determines the effects of the particular wireless device application on the treatment costs of the one or more diseases.

8. The method of claim 1, wherein retrieving the patient population information comprises:
   tracking usage information of a reconciled regimen of wireless device applications by the patient population; and
   retrieving the tracked usage information.

9. The method of claim 8, wherein tracking the usage information of a reconciled regimen of wireless device applications comprises tracking the usage information of wireless device applications from more than one wireless device application providers.

10. The method of claim 1, wherein organizing the data reports further comprises filtering patients from the patient population in one or more data sets based on one or more sets of demographic attributes, and wherein the analyzing the data sets comprises comparing a data set including patients with a first set of demographic attributes to a data set including patients with a second set of demographic attributes to determine the different effects of providing a given wireless device application to patients with the first set of demographic attributes and the patients with the second set of demographic attributes.

11. The method of claim 1, further comprising presenting the determination to a physician for use in making a treatment or clinical decision.

12. A system comprising:
one or more computers and one or more storage devices storing instructions that are operable, when executed by the one or more computers, to cause the one or more computers to perform operations comprising:
receiving via a communications network, by an analytic server, one or more data reports from one or more wireless device application providers that provide wireless device applications to patients, each data report comprising an anonymized patient identifier that identifies a patient associated with the data report, and a wireless device application identifier that identifies the wireless device application discussed by the data report, wherein the wireless device application has been prescribed by a healthcare professional to aid in the treatment of one or more medical conditions of the patient and wherein the wireless device application is configured to track physiologic parameters of the patient;
decoding, by the analytic server, the one or more data reports to retrieve, for a given data report, the anonymized patient identifier as well as the corresponding wireless device application identifier;
retrieving via the communications network, by the analytic server, patient population information solely using the decoded anonymized patient identifier associated with each data report, the patient population information comprising electronic medical information associated with a patient population to whom more than one wireless device applications were provided;
merging data reports to generate data sets based on the retrieved patient population information associated with the patient population to whom a particular wireless device application has been provided, such that each data set is instantaneously generated and only includes data reports associated with the same wireless device application identifier and identified solely through the anonymized patient identifier; and
analyzing the data sets and the patient population information to determine the impact of each wireless device application from the more than one wireless device applications on managing the treatment of the one of more medical conditions across cohorts of patients without jeopardizing each patient's privacy when a first cohort of patients with a given condition who have received a particular wireless device application in addition to a regular treatment is compared to a second cohort of patients with the given condition who have received the regular treatment but without the particular wireless device application to determine an improved adherence to the regular treatment when the regular treatment is combined with the particular wireless device application.

13. The system of claim 12, wherein determining the impact of a wireless device application on managing the treatment of the one of more medical conditions includes generating quantitative information about the impact of the wireless device application on managing the treatment of the one of more medical conditions between the first cohort of patients and the second cohort of patients by virtue of a statistically different physiologic parameter being tracked by the wireless device application.

14. The system of claim 12, wherein the analyzing comprises comparing a characteristic of a data set in which the particular wireless device application was provided to a characteristic of a control set that includes members of the patient population that were not using the particular wireless device application.

15. The system of claim 12, wherein receiving the one or more data reports further comprises receiving for each data report a corresponding provider identifier that identifies the wireless device application provider associated with the data report, the retrieving further retrieves provider information associated with each data report using the corresponding provider identifier associated with the data report, and the analyzing further uses the provider information to determine the effects of providing a given wireless device application.

16. The system of claim 12, wherein retrieving the patient population information includes retrieving information about treatment outcomes for the medical conditions of the patient population, and the analyzing determines the effects of the particular wireless device application on the treatment outcomes of the one or more medical conditions.

17. The system of claim 12, wherein retrieving the patient population information includes retrieving information about treatment outcomes for the medical conditions of the patient population and a drug, medical device, or other therapy prescribed to the patient population, and the analyzing determines the effects of coadminstruction of the wireless device application, the drug, the medical device, or other therapy on the treatment outcomes of the one or more medical conditions.

18. The system of claim 12, wherein retrieving the patient population information includes retrieving information about treatment costs for the medical conditions of the patient population, and the analyzing determines about the effects of the particular wireless device application on the treatment costs of the one or more diseases.

19. The system of claim 12, wherein retrieving the patient population information comprises the operations of:
tracking usage information of a reconciled regiment of wireless device applications by the patient population; and
retrieving the tracked usage information.

20. The system of claim 19, wherein tracking the usage information of a reconciled regiment of wireless device applications comprises the operation of tracking the usage information of wireless device applications from more than one wireless device application providers.

21. The system of claim 12, wherein organizing the data reports further comprises filtering patients from the patient population in one or more data sets based on one or more sets of demographic attributes, and wherein the analyzing the data sets comprises comparing a data set including patients with a first set of demographic attributes to a data set including patients with a second set of demographic attributes to determine the different effects of providing a given wireless device application to patients with the first set of demographic attributes and the patients with the second set of demographic attributes.

22. The system of claim 12, the operations further comprising presenting the determination to a physician for use in making a treatment or clinical decision.

23. A non-transitory computer-readable storage device storing software comprising instructions executable by one or more computers which, upon such execution, cause the one or more computers to perform operations comprising:
receiving via a communications network, by an analytic server, one or more data reports from one or more wireless device application providers that provide wireless device applications to patients, each data report comprising an anonymized patient identifier that identifies a patient associated with the data report, and a wireless device application identifier that identifies the wireless device application discussed by the data report, wherein the wireless device application has been prescribed by a healthcare professional to aid in the treatment of one or more medical conditions of the patient and wherein the wireless device application is configured to track physiologic parameters of the patient;

decoding, by the analytic server, the one or more data reports to retrieve, for a given data report, the anonymized patient identifier as well as the corresponding wireless device application identifier;

retrieving via the communications network, by the analytic server, patient population information solely using the decoded anonymized patient identifier associated with each data report, the patient population information comprising electronic medical information associated with a patient population to whom more than one wireless device applications were provided;

merging data reports to generate data sets based on the retrieved patient population information associated with the patient population to whom a particular wireless device application has been provided, such that each data set is instantaneously generated and only includes data reports associated with the same wireless device application identifier and identified solely through the anonymized patient identifier; and analyzing the data sets and the patient population information to determine the impact of each wireless device application from the more than one wireless device applications on managing the treatment of the one of more medical conditions across cohorts of patients without jeopardizing each patient's privacy when a first cohort of patients with a given condition who have received a particular wireless device application in addition to a regular treatment is compared to a second cohort of patients with the given condition who have received the regular treatment but without the particular wireless device application to determine an improved adherence to the regular treatment when the regular treatment is combined with the particular wireless device application to determine an improved adherence to the regular treatment when the regular treatment is combined with the particular wireless device application.

24. The computer-readable storage device of claim 23, wherein determining the impact of a wireless device application on managing the treatment of the one of more medical conditions includes generating quantitative information about the impact of the wireless device application on managing the treatment of the one of more medical conditions between the first cohort of patients and the second cohort of patients by virtue of a statistically different physiologic parameter being tracked by the wireless device application.

25. The computer-readable storage device of claim 23, wherein the analyzing comprises comparing a characteristic of a data set in which particular wireless device application was provided to a characteristic of a control set that includes members of the patient population that were not using the particular wireless device application.

26. The computer-readable storage device of claim 23, wherein receiving the one or more data reports further comprises receiving for each data report a corresponding provider identifier that identifies the wireless device application provider associated with the data report, the retrieving further retrieves provider information associated with each data report using the corresponding provider identifier associated with the data report, and the analyzing further uses the provider information to determine the effects of providing a given wireless device application.

27. The computer-readable storage device of claim 23, wherein retrieving the patient population information includes retrieving information about treatment outcomes for the medical conditions of the patient population, and the analyzing determines the effects of the particular wireless device application on the treatment outcomes of the one or more medical conditions.

28. The computer-readable storage device of claim 23, wherein retrieving the patient population information includes retrieving information about treatment outcomes for the medical conditions of the patient population and a drug, medical device, or other therapy prescribed to the patient population, and the analyzing determines the effects of coadminstruction of the wireless device application the drug, the medical device, or other therapy on the treatment outcomes of the one or more medical conditions.

29. The computer-readable storage device of claim 23, wherein retrieving the patient population information includes retrieving information about treatment costs for the medical conditions of the patient population, and the analyzing determines the effects of the particular wireless device application on the treatment costs of the one or more diseases.

30. The computer-readable storage device of claim 23, wherein retrieving the patient population information comprises the operations of:
  tracking usage information of a reconciled regimen of wireless device applications by the patient population; and
  retrieving the tracked usage information.

31. The computer-readable storage device of claim 30, wherein tracking the usage information of a reconciled regimen of wireless device applications comprises the operation of tracking the usage information of wireless device applications from more than one wireless device application providers.

32. The computer-readable storage device of claim 23, wherein organizing the data reports further comprises filtering patients from the patient population in one or more data sets based on one or more sets of demographic attributes, and wherein the analyzing the data sets comprises comparing a data set including patients with a first set of demographic attributes to a data set including patients with a second set of demographic attributes to —determines the different effects of providing a given wireless device application to patients with the first set of demographic attributes and the patients with the second set of demographic attributes.

33. The computer-readable storage device of claim 23, the operations further comprising presenting the determination to a physician for use in making a treatment or clinical decision.

* * * * *

UNITED STATES PATENT AND TRADEMARK OFFICE
CERTIFICATE OF CORRECTION

PATENT NO. : 9,910,963 B2
APPLICATION NO. : 13/933405
DATED : March 6, 2018
INVENTOR(S) : Brad Ryan et al.

Page 1 of 1

It is certified that error appears in the above-identified patent and that said Letters Patent is hereby corrected as shown below:

In the Claims

Column 22, Line 32, Claim 6, please delete "coadminstruction" and insert therefor
-- coadministration --;

Column 24, Line 24, Claim 17, please delete "coadminstruction" and insert therefor
-- coadministration --;

Column 26, Line 24, Claim 28, please delete "coadminstruction" and insert therefor
-- coadministration --; and Column 26, Line 54, Claim 32, please delete "—determines" and insert therefor -- determines --.

Signed and Sealed this
Fifteenth Day of January, 2019

Andrei Iancu
*Director of the United States Patent and Trademark Office*